(12) United States Patent
Shkolnikov et al.

(10) Patent No.: US 11,543,356 B2
(45) Date of Patent: *Jan. 3, 2023

(54) ROTATION AND FLAT-FORM IMAGING FOR MICROSCOPIC OBJECTS

(71) Applicant: Hewlett-Packard Development Company, L.P., Spring, TX (US)

(72) Inventors: Viktor Shkolnikov, Palo Alto, CA (US); Fausto D'Apuzzo, Palo Alto, CA (US); Yang Lei, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/256,681

(22) PCT Filed: Oct. 29, 2018

(86) PCT No.: PCT/US2018/058017
§ 371 (c)(1),
(2) Date: Dec. 29, 2020

(87) PCT Pub. No.: WO2020/091732
PCT Pub. Date: May 7, 2020

(65) Prior Publication Data
US 2021/0262937 A1 Aug. 26, 2021

(51) Int. Cl.
*G01N 21/64* (2006.01)
*B01L 3/00* (2006.01)
(Continued)

(52) U.S. Cl.
CPC ...... *G01N 21/6454* (2013.01); *B01L 3/50853* (2013.01); *G02B 21/06* (2013.01); *G02B 21/365* (2013.01); *B01L 2300/0829* (2013.01)

(58) Field of Classification Search
CPC .............. G01N 21/6454; G01N 21/253; B01L 3/50853; B01L 2300/0829; G02B 21/06; G02B 21/365; C12M 23/12; C12M 41/36
See application file for complete search history.

(56) References Cited

U.S. PATENT DOCUMENTS

| 6,083,763 A * | 7/2000 | Balch ..................... B01L 3/5085 436/524 |
| 6,969,449 B2 * | 11/2005 | Maher ................ G01N 33/5044 204/403.01 |

(Continued)

FOREIGN PATENT DOCUMENTS

| CN | 206292164 | 6/2017 |
| EP | 2639292 | 9/2013 |

(Continued)

OTHER PUBLICATIONS

Ikbal Sencan "Lensfree Computational Microscopy Tools and their Biomedical Applications", Dissertation, 2013 (Year: 2013).*

(Continued)

*Primary Examiner* — Richard A Hansell, Jr.
(74) *Attorney, Agent, or Firm* — Foley & Lardner LLP

(57) ABSTRACT

An example apparatus includes a well plate having an array of wells, a light encoding layer positioned under the well plate, an imaging layer to capture an image of the well plate encoded by the light encoding layer, an array of electrodes positioned on a surface of a bottom floor of the at least one well, and a controller. The light encoding layer is to encode light passing through a microscopic object in at least one well of the array of wells. The light encoding layer has a substantially flat form. The controller is to direct electrical voltage to the electrodes to generate a non-rotating, non-uniform electrical field, the electrical field being to rotate an object in the electrical field.

20 Claims, 8 Drawing Sheets

(51) Int. Cl.
G02B 21/06 (2006.01)
G02B 21/36 (2006.01)

(56) References Cited

U.S. PATENT DOCUMENTS

| | | | |
|---|---|---|---|
| 11,170,200 B2* | 11/2021 | Kim | G06V 10/82 |
| 2006/0126921 A1* | 6/2006 | Shorte | G02B 21/22 |
| | | | 382/154 |
| 2016/0041094 A1 | 2/2016 | Lei | |
| 2018/0136114 A1* | 5/2018 | Delattre | G01N 21/17 |
| 2019/0143316 A1* | 5/2019 | Hammerstad | B01L 3/0237 |
| | | | 73/1.73 |
| 2020/0159002 A1* | 5/2020 | Matsunaga | C12M 23/16 |

FOREIGN PATENT DOCUMENTS

| | | | | |
|---|---|---|---|---|
| JP | 2009204451 | 9/2009 | | |
| WO | WO-2003001889 | 1/2003 | | |
| WO | WO-2009020506 A1 * | 2/2009 | | G01N 33/5434 |
| WO | WO-2015144608 | 10/2015 | | |
| WO | WO-2015185341 | 12/2015 | | |
| WO | WO-2018013100 A1 * | 1/2018 | | B01L 3/0237 |
| WO | WO-2018023039 | 2/2018 | | |

OTHER PUBLICATIONS

Khorasaninejad, Mohammadreza, et al. "Metalenses at visible wavelengths: Diffraction-limited focusing and subwavelength resolution imaging." Science 352, No. 6290 (2016): 1190-1194.
Wu, Yichen, et al. "Lensless digital holographic microscopy and its applications in biomedicine and environmental monitoring." Methods 136 (2018): 4-16.

* cited by examiner

ROTATION AND FLAT-FORM IMAGING FOR MICROSCOPIC OBJECTS

BACKGROUND

Analysis of biological material, such as cells, is performed for a variety of applications. Analysis is often performed by isolating biological material, such as cells or type of cells, and taking an image of the biological material. The image may be taken using, for example, a microscope. The image may then be analyzed for identification or detection of various features of the biological material.

BRIEF DESCRIPTION OF THE DRAWINGS

For a more complete understanding of various examples, reference is now made to the following description taken in connection with the accompanying drawings in which.

DETAILED DESCRIPTION

As noted above, analysis of biological material often includes imaging of the biological material. Such imaging often results in imaging of a single sample or a small number of samples. Thus, monitoring of reactions, for example, may be limited to a few samples at any one time, resulting in long sample-to-result times. Further, imaging systems are often large due to the desired amplification of the samples. For example, a microscope with a long focal length may be employed to image a microscopic sample.

In various examples, cells in a well plate with multiple wells may be imaged or monitored with a flat-form imaging arrangement. In one example, the well plate is provided with a light encoding layer and an imaging layer. The light imaging layer may be a lens-less layer to provide computational imaging (e.g., an amplitude mask or a diffuser) or a flat-lens array (e.g., meta-lens array). The light encoding layer may encode the light from a light source passing through the cells in the well plate. The raw imaging data may be captured by the imaging layer, which may include a CCD or a CMOS layer. The use of a flat-form light encoding layer provides a large field of view for the imaging layer, allowing simultaneous imaging or monitoring of a well plate with a large number of wells. Each well is provided with an array of electrodes to generate a non-uniform, non-rotating electric field. The electric field creates an electrical torque to cause microscopic objects in the wells to rotate. Thus, the microscopic object may be imaged from multiple directions.

Figure 1:
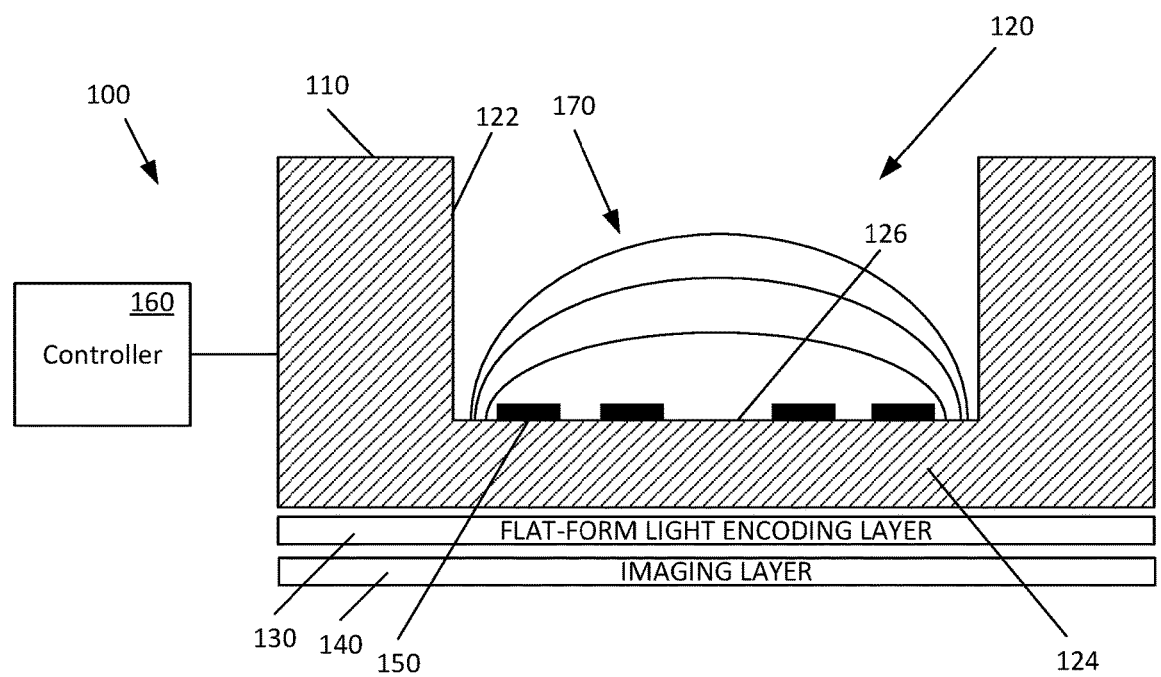
FIG. 1 is a cross-sectional side view of an example apparatus for flat-form imaging.

Referring now to the Figures, a cross-sectional side view of an example apparatus 100 for flat-form imaging is illustrated. The example apparatus includes a well plate 110 which includes an array of wells 120. In various examples, the well plate 110 may include any number of wells 120. In the example illustrated in FIG. 1, the array of wells 120 includes a single well. In other examples, the number of wells 120 may be as large as practically possible. In various examples, the well 120 may have any of a variety of shapes. In the example of FIG. 1, the well 120 is defined by a side wall 122 and a bottom floor 124. The bottom floor 124 has an internal surface 126 defining the interior of the well 120.

The size and shape of each well 120 may be selected from any of a variety of sizes and shapes. In one example, the wells 120 are cylindrical with a cross section that may be circular, rectangular, hexagonal or any of a variety of other shapes. In other examples, each well 120 is conical or other non-cylindrical shape. In one example, each well 120 is a circular cylinder with a diameter of between 1 mm and 100 mm.

The wells 120 are provided to position microscopic objects (not shown) therein. The well plate 110 may be formed of any of a variety of materials such as, for example, plastics or glasses. In one example, the well plate 110 is formed of a non-reactive material, such as polypropylene. The well plate 110 may be of any practical size according to a desired application. For example, the well plate 110 may be sized to accommodate a specific number of wells 120, each of which may be provided to position the microscopic objects therein. The microscopic objects may include any of a variety of objects such as cells or biological reagents, for example.

The example apparatus 100 of FIG. 1 is provided with a light encoding layer 130. The light encoding layer 130 of the example apparatus 100 has a substantially flat form. For example, the light encoding layer 130 may include a flat-form, lens-less computational imaging layer which may include an amplitude mask or a diffuser, as described below with reference to FIG. 8, or a substantially flat array of lenses (e.g., meta-lens array), as described below with reference to FIG. 9. The flat-form nature of the light encoding layer 130 facilitates a wide field of view which can allow encoding of light over a large area simultaneously. In this regard, light passing through a large number of microscopic objects on a relatively large area of the well plate 110 can be simultaneously encoded.

The example apparatus 100 of FIG. 1 further includes an imaging layer 140 to capture an image encoded by the light encoding layer 130. As noted above, the image encoded by the light encoding layer 130 is the collection of light passing through the well plate 110 and any microscopic objects on the well plate 110. In this regard, the imaging layer 140 is able to capture an image of a wide field of view, as encoded by the light encoding layer 130. In various examples, the imaging layer may include a charge-coupled device (CCD) or a complementary metal-oxide semiconductor (CMOS) device, for example. Thus, the example apparatus 100 is able to image a wide field of view with a flat form.

The example apparatus 100 of FIG. 1 is further provided with an array of electrodes 150 positioned on the surface 126 of the bottom floor 124 of the well 120. A controller 160 is provided to direct an electrical voltage to the electrodes 150 from a power source (not shown in FIG. 1). In various examples, the power source is an alternating current (AC)

power source. The electrical voltage causes the electrodes 150 to generate an electrical field 170 in the well 120. In various examples, the electrical field 170 is a non-rotating, non-uniform electrical field. The non-rotating, non-uniform electrical field 170 is provided to rotate an object in the electrical field, as described below in greater detail with reference to FIG. 4.

Figure 2:
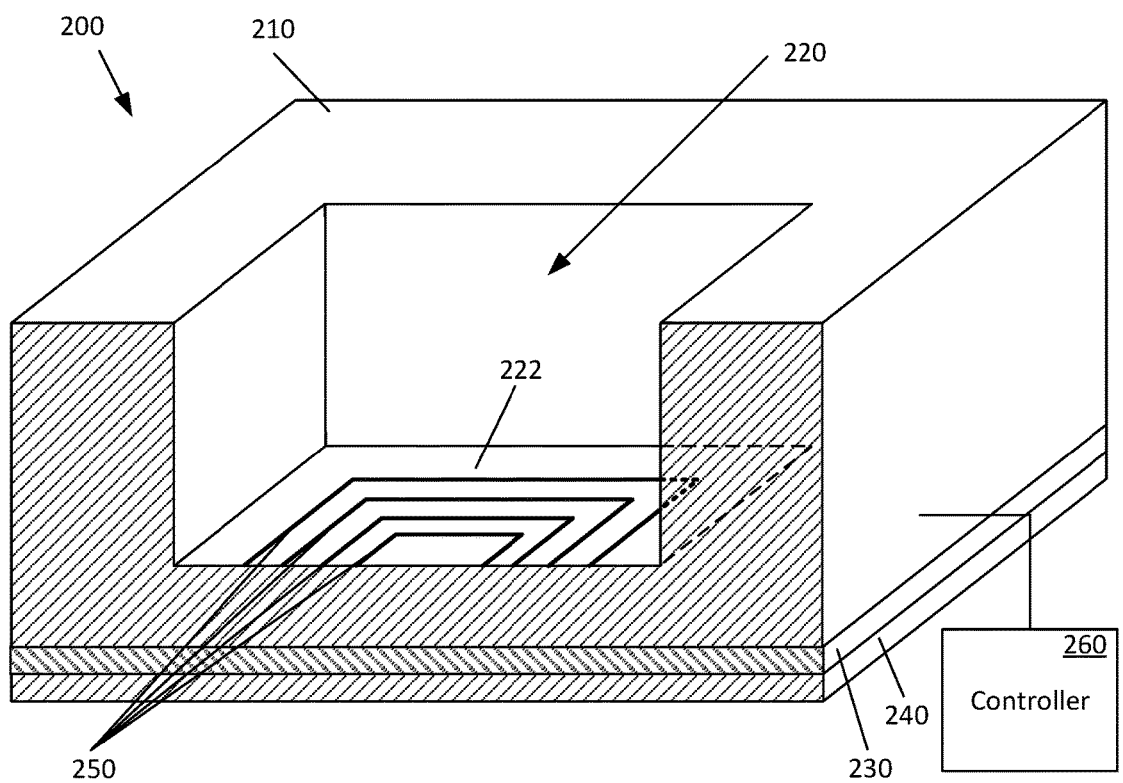
FIG. 2 is a cross-sectional perspective view of another example apparatus for flat-form imaging.

Referring now to FIG. 2, a cross-sectional perspective view of another example apparatus 200 is illustrated. The example apparatus 200 is similar to the example apparatus 100 of FIG. 1 and includes a well plate 210 with at least one well 220. The example apparatus 200 of FIG. 2 further includes a light encoding layer 230 and an imaging layer 240, similar to the layers 130, 140 described above with reference to FIG. 1. As noted above, the well 220 may have any of a variety of shapes. In the example apparatus 200 of FIG. 2, the well 220 is formed as a rectangular prism with a rectangular bottom surface 222.

The example apparatus 200 is provided with an array of electrodes 250 on the bottom surface 222 of the well 220. As described above, a controller 260 is provided to direct an electrical voltage to the electrodes 250 from an AC power source. The array of electrodes 250 may be positioned in a variety of manners. In certain examples, the electrodes 250 are arranged in a concentric formation. For example, in the example apparatus 200 of FIG. 2, the electrodes 250 are rectangular electrodes arranged concentrically to one another. In other examples, the electrodes may be arranged as concentric circles, concentric hexagons, or the like. The concentric electrodes are arranged to generate an electrical field that is non-rotating and non-uniform.

Figure 3:
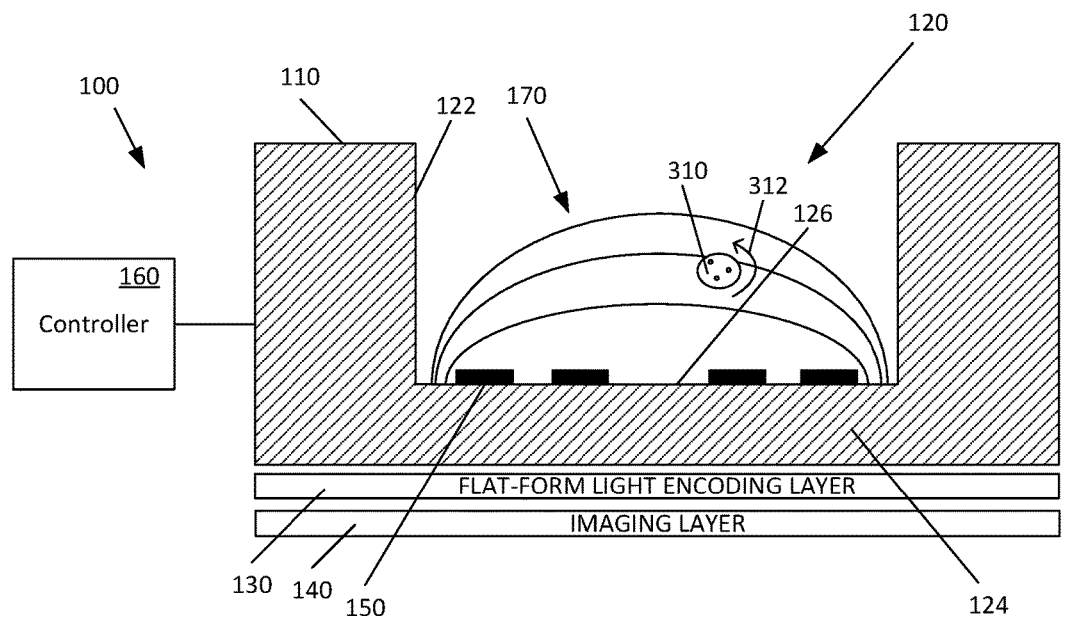
FIG. 3 is a cross-sectional side view of the example apparatus of FIG. 1 with an object to be imaged.

Referring now to FIG. 3, a cross-sectional side view of the example apparatus of FIG. 1 is illustrated with an object to be imaged. As noted above, the example apparatus 100 of FIG. 1 is provided with an array of electrodes 150 to generate an electrical field 170 in the well 120. In various examples, the electrical field 170 is a non-rotating, non-uniform electrical field and is provided to rotate an object in the electrical field. As illustrated in FIG. 3, an object 310 (e.g., cell) may be positioned within the electrical field 170. The arrangement of the electrodes 150 allows the electrical field 170 to be non-rotating while allowing the electrical field 170 to cause rotation of the object 310 within the electrical field 170, as indicated by the arrow 312 in FIG. 3 and as described below with reference to FIG. 4.

Figure 4:
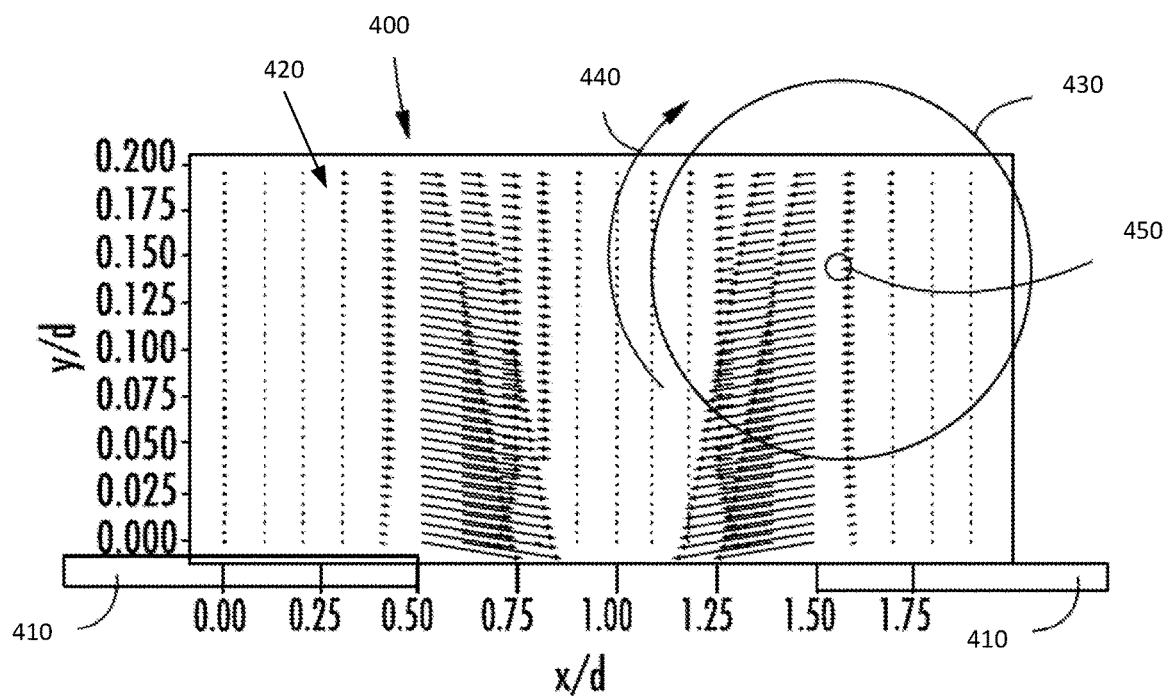
FIG. 4 is a cross-sectional side view of an example well with an electrical field to rotate an object.

FIG. 4 is a cross-sectional side view of an example well with an electrical field to rotate an object. FIG. 4 illustrates a well 400 with electrodes 410 positioned on a bottom surface. As noted above, the electrodes 410 are provided to generate a non-rotating, non-uniform electrical field 420.

In one example, the electrical field produces a traveling wave dielectrophoresis (DEP) force in at least two directions. While electrophoresis moves particles with the particles themselves electrically charged, DEP results in movement of the particles without the need for charges on the particles. Further, while stationary DEP relies on an electrical field from adjacent electrodes having AC voltage at different frequencies, traveling wave DEP may achieve movement of particles with AC voltage applied to electrodes that are spaced apart (e.g., parallel or concentric) with a phase offset. In some examples, phase offset cycles through a 360-degree shift over a number of electrodes, such as four electrodes with adjacent electrodes having a 90-degree phase offset. For example, the traveling wave DEP force may be generated by applying voltage to the electrodes with phase variations. The phase variations result in the force in a direction based on the direction of the phase offset. Thus, the particle travels in the direction of the phase variation. In other words, the particle travels where the wave generated by the offset travels. As described in various examples above, the electrodes may be arranged in a concentric manner.

In one example, the voltage applied to the electrodes 410 may be temporally constant. Thus, the electrical field in the well is generated by a temporally constant AC profile applied to the various electrodes 410. Of course, those skilled in the art will appreciate that an alternating current varies within a cycle. In this regard, a "constant" AC voltage refers to a voltage with a constant peak-to-peak voltage.

Referring again to FIG. 4, the non-uniform nature of the electrical field can result in an electrical torque applied to an object 430 in the electrical field 420 when the object 430 is near an electrode (e.g., electrodes 410) so as to rotate the object about a rotational axis 450 parallel to the edge of the electrode. As indicated by the length of the field lines in FIG. 4, one portion of the object 430 may experience a relatively strong electrical field (e.g., the bottom portion of the object 430), while another portion of the objet 430 may experience a relatively weak electrical field (e.g., the top portion of the object 430). Thus, the non-uniform electrical field 420 can result in a torque on the object 430, causing the object to rotate, as indicated by the arrow 440 about the axis 450. In various examples, the orientation of the electrical field may be controlled such that the axis of rotation 450 can be aligned in different positions to selectively rotate the object. In this manner, the object 430 can be imaged from any desired direction.

The rotation of the object 430 facilitates the capturing of images of the object 430 from different angles to facilitate three-dimensional reconstruction or modeling of cellular object 430 for analysis. Capturing of 2D images at various angles can allow for a transformation of the pixels at various angles into 3D voxels representing the object 430. One example method of such transformation is described below with reference to FIG. 5.

Figure 5:
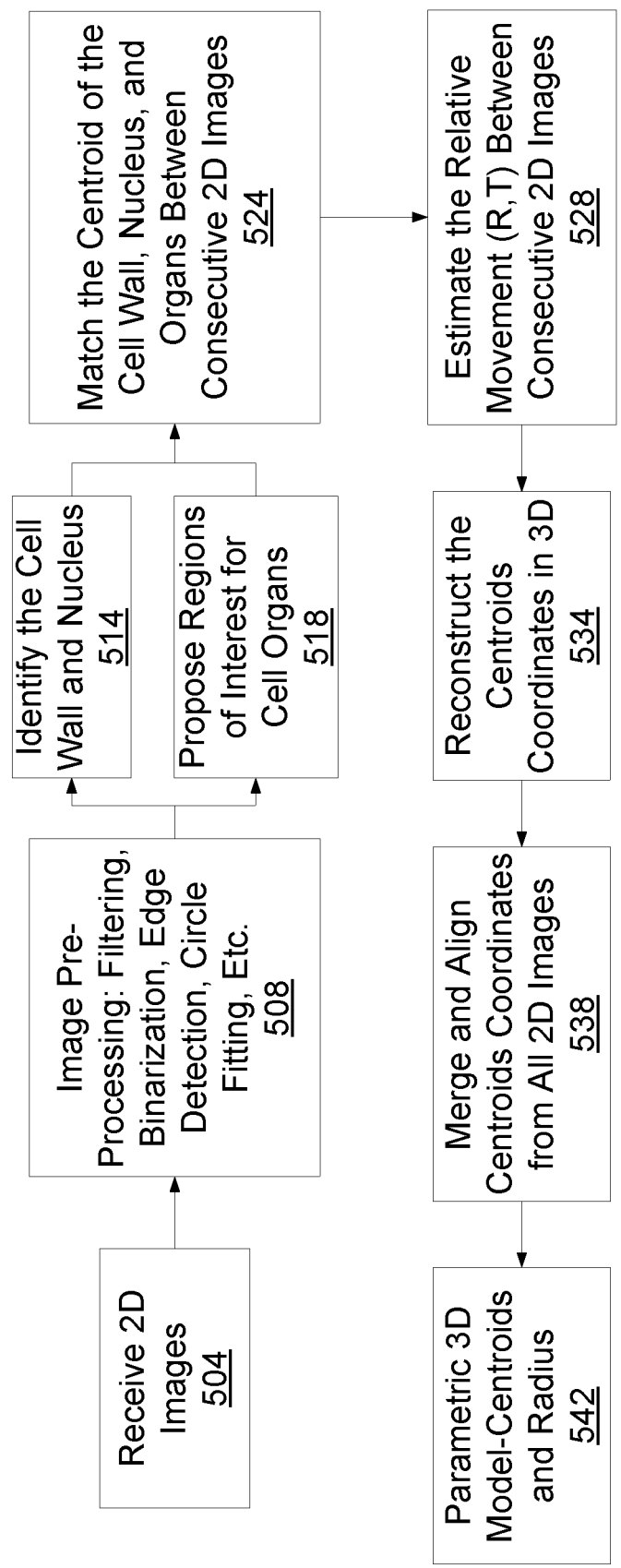
FIG. 5 is flow chart illustrating an example three-dimensional volume modeling method.

FIG. 5 is a flow chart of an example three-dimensional volumetric modeling method 500. The example method 500 of FIG. 5 is described below with reference to the example system 100 described above with reference to FIG. 3. In this regard, the example method 500 may be carried out by a controller, such as the controller 160 of FIG. 3, using captured two-dimensional images of the rotating object 310. As indicated by block 504, the controller 160 receives video frames or two-dimensional images captured by the imaging layer 140 during rotation of object 310. As indicated by block 508, various pre-processing actions are taken with respect to the received two-dimensional images. Such pre-processing may include filtering, binarization, edge detection, circle fitting and the like.

As indicated by block 514, utilizing such edge detection, circle fitting and the like, controller 160 retrieves and consults a predefined three-dimensional volumetric template of the object 310, to identify various internal structures of the object are various internal points in the object. The three-dimensional volumetric template may identify the shape, size and general expected position of internal structures which may then be matched to those of the two-dimensional images taken at the different angles. For example, a single cell may have a three-dimensional volumetric template comprising a sphere having a centroid and a radius. The three-dimensional location of the centroid and radius are determined by analyzing multiple two-dimensional images taken at different angles.

Based upon a centroid and radius of the biological object or cell, the controller 160 may model in three-dimensional space the size and internal depth/location of internal structures, such as the nucleus and organelles. For example, with respect to cells, the controller 160 may utilize a predefined template of a cell to identify the cell wall and the nucleus. As indicated by block 518 of FIG. 5, using a predefined template, the controller 160 additionally identifies regions or points of interest, such as organs or organelles of the cell. As indicated by block 524, the controller 160 matches the centroid of the cell membrane, nucleus and organelles amongst or between the consecutive frames so as to estimate the relative movement (R, T) between the consecutive frames per block 528.

As indicated by block 534, based upon the estimated relative movement between consecutive frames, the controller 160 reconstructs the centroid coordinates in three-dimensional space. As indicated by block 538, the centroid three-dimensional coordinates reconstructed from every two frames are merged and aligned. A single copy of the same organelle is preserved. As indicated by block 542, the controller 160 outputs a three-dimensional volumetric parametric model of object 310.

Figure 6:
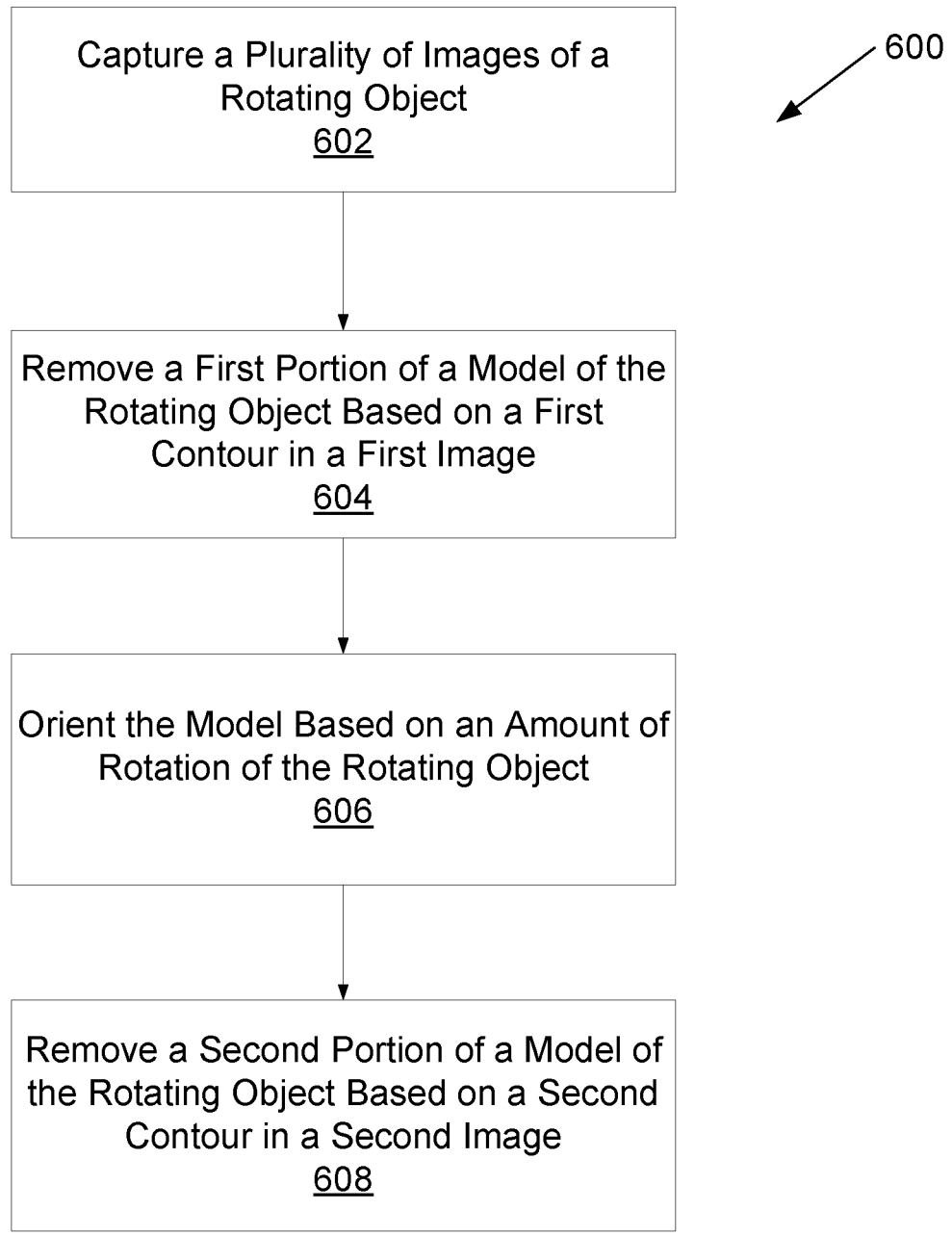
FIG. 6 is a flow chart of another example method to generate a three-dimensional model of an object from images of the object.

Referring now to FIG. 6, a flow chart illustrating another example method 600 to generate a model of an object from images of the object is provided. A processor may perform elements of the method 600. At block 602, the method 600 may include capturing a plurality of images of a rotating object using the flat-form encoding 130 and imaging 140 layers described previously with reference to FIGS. 1 and 3. The images may be captured over time, and the object may rotate into different orientations between images.

Block 604 may include removing a first portion of a model of the rotating object based on a first contour of the rotating object in a first image of the plurality of images. For example, the first portion to be removed may be determined based on the first contour. The first portion may be a portion outside the first contour or a portion inside the first contour. At block 606, the method 600 may include orienting the model based on an amount of rotation of the rotating object between capture of the first image and capture of a second image of the plurality of images. Orienting the model may include rotating the model, determining a location of an image plane relative to the model, selecting a projection direction based on the amount of rotation of the rotating object, or the like.

Block 608 may include removing a second portion of the model of the rotating object based on a second contour of the rotating object in the second image. For example, the second portion to be removed may be determined based on the second contour. In some examples, the first and second portions to be removed may both be determined before either is actually removed from the model. In an example, the first portion may be removed from the model prior to determination of the second portion to be removed.

Figure 7:
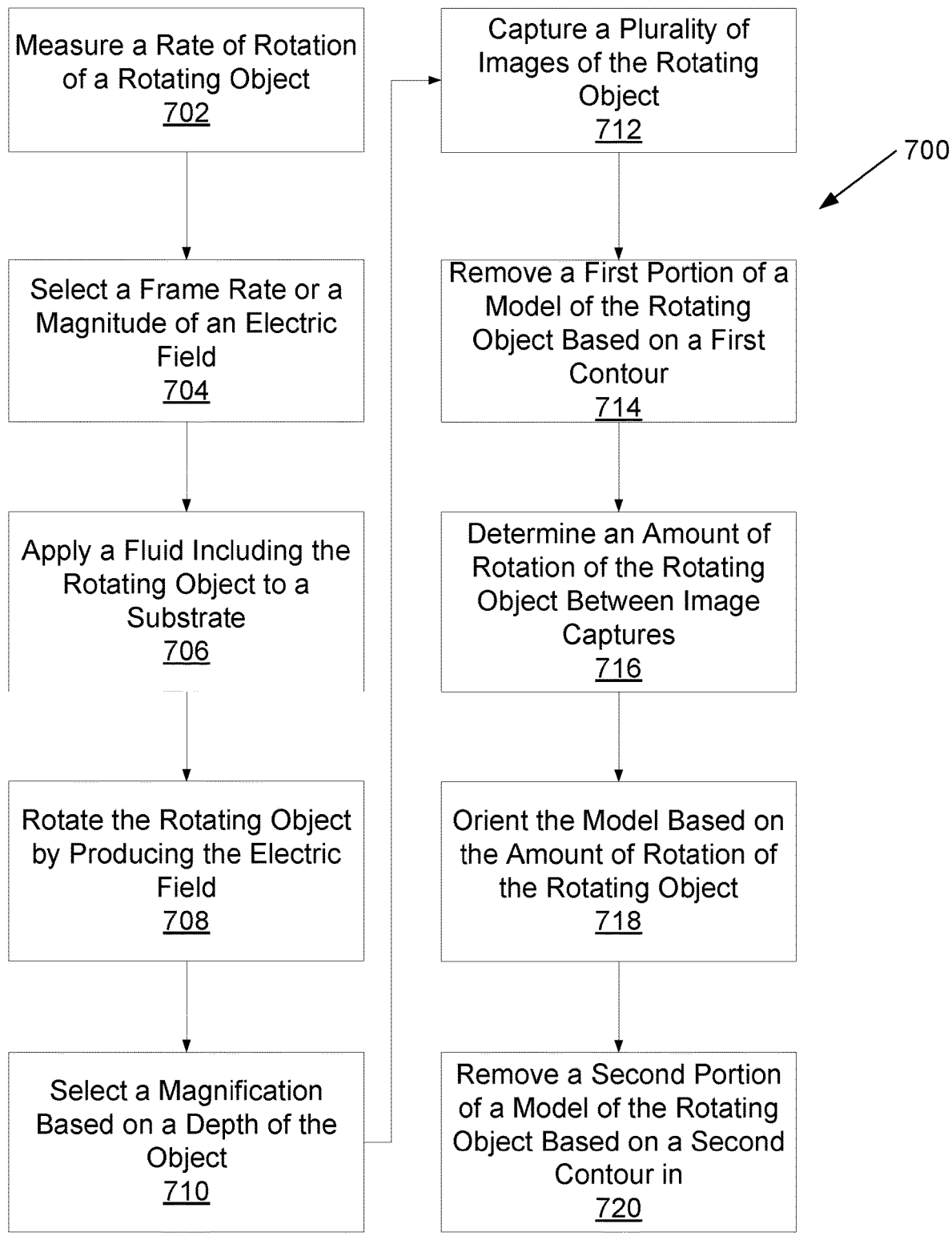
FIG. 7 is a flow chart of another example method to generate a three-dimensional model of an object from images of the object.

Referring now to FIG. 7, a flow chart illustrating another example method 700 to generate a model of an object from images of the object is provided. A processor may perform elements of the method 700. At block 702, the method 700 may include measuring a rate of rotation of a rotating object. In an example, the object may be subjected to rotational forces of various magnitudes, such as electric field induced by signals with various voltages or frequencies. The rate of rotation may be measured to determine how the choice of parameters related to application of the rotational force affect the rate of rotation (e.g., to allow parameters to be chosen to produce a desired rate of rotation). In some examples, a set of parameters related to application of the rotational force may be chosen, and the rate of rotation may be measured and stored for use during later elements of the method 700.

Block 704 may include selecting a frame rate of an imaging device based on a rate of rotation of a rotating object or selecting a magnitude of a nonrotating, nonuniform electric field to cause a rate of rotation selected based on a frame rate of the imaging device. For example, based on the rate of rotation, the frame rate may be selected to result in a desired amount of rotation of the rotating object between captured images. In some examples, the frame rate may be fixed or set to a predetermined value, and the magnitude of an electric field to rotate the rotating object may be selected based on that frame rate. In some examples, the electric field may be a nonrotating, nonuniform electric field that causes rotation of the rotating object. The magnitude of the electric field, such as the voltage applied to electrodes to induce the electric field, a frequency of the applied voltage, or the like, may be selected based on a desired rate of rotation of the rotating object. The desired rate of rotation may be selected based on the frame rate, for example, to produce a desired amount of rotation of the rotating object between captured images. The relationship between frequency or voltage and rate of rotation may be determined from the measurements at block 702, may be calculated based on assumptions about the rotating object, or the like. In an example, the frame rate or voltage or frequency of the electric field may be selected without regard to the rate of rotation of the rotating object.

At block 706, the method 700 may include applying a fluid in which the rotating object is suspended to a substrate. For example, the rotating object may be mixed with the fluid or may have been previously stored in the fluid. The fluid may be applied to the substrate by pipetting, jetting, or the like. The rotating object may not be rotating initially when it is suspended in the fluid or applied to the substrate. Block 708 may include rotating the rotating object by producing a nonrotating, nonuniform electric field using a plurality of electrodes on the substrate. Producing the nonrotating, nonuniform electric field may include applying an AC voltage to a plurality of electrodes in or on the substrate (e.g., electrodes beneath the fluid). The voltage or frequency of the AC voltage may be selected at block 704, may be predetermined, or the like. In some examples, measuring the rate of rotation at block 702 may be performed after block 708, such as when the voltage or frequency of the AC voltage are not selected to produce a predetermined or design rate of rotation.

At block 710, the method 700 may include designing the light encoding layer to provide a desired magnification. The magnification may be selected so that the rotating object can be imaged with a depth of field that is at least substantially a depth of the object. For example, higher magnifications may result in smaller depths of field, so the highest magnification that results in an acceptable depth of field may be used.

Block 712 may include capturing a plurality of images of the rotating object using the imaging device, which is optically coupled light encoding layer. For the imaging device may be instructed to capture a plurality of images, may be triggered at periodic intervals to capture the plurality of images, or the like. At block 714, the method 700 may include removing a first portion of a model of the rotating object based on a first contour of the rotating object in a first image of the plurality of images. For example, removing the first portion may include determining the first portion to be removed, or removing the determined first portion. In an example, determining the first portion to be removed may include determining a first voxel to be removed.

Block 716 may include determining the amount of rotation of the rotating object between capture of the first image and capture of a second image of the plurality of images based on the rate of rotation. The rate of rotation may have been measured at block 708, may have been calculated (e.g., based on characteristics of the object, characteristics of the force or field causing rotation, the voltage or frequency applied to an electrode to create an electric field, etc.), may have been set by choosing parameters related to generation of a force or field causing rotation (e.g., the voltage or frequency applied to an electrode to create an electric field, a magnitude of a field or force causing rotation, etc.), or the like. The amount of rotation may be determined based on the rate of rotation and the timing of the first and second images (e.g., the frame rate, the time between capturing of the first and second images, or the like).

Block 718 may include orienting the model based on the amount of rotation of the rotating object between capture of the first image and capture of the second image. Orienting the model may include rotating the model, determining a location of an image plane relative to the model, selecting a projection direction based on the amount of rotation of the rotating object, or the like. For example, the model may be rotated the same amount the object rotated, or the image plane or projection direction may have rotated the same amount as the object but in an opposite direction when the model is stationary.

Block 720 may include removing a second portion of the model of the rotating object based on a second contour of the rotating object in the second image. As with block 714, removing the second portion may include determining the second portion to be removed, and removing the determined second portion. Determining the second portion to be removed may include determining a second voxel to be removed. In an example, both the first portion and the second portion may be determined before either portion is removed. For example, each contour may be compared to the model to determine which portions to remove. In some examples, the comparisons of multiple contours to the model may be used to determine whether a particular portion (e.g., a particular voxel) can be removed. In some examples, the first portion may be removed before the second portion is determined. In some examples, blocks of the method 700 may be repeated to iteratively remove portions of the model.

Figure 8:
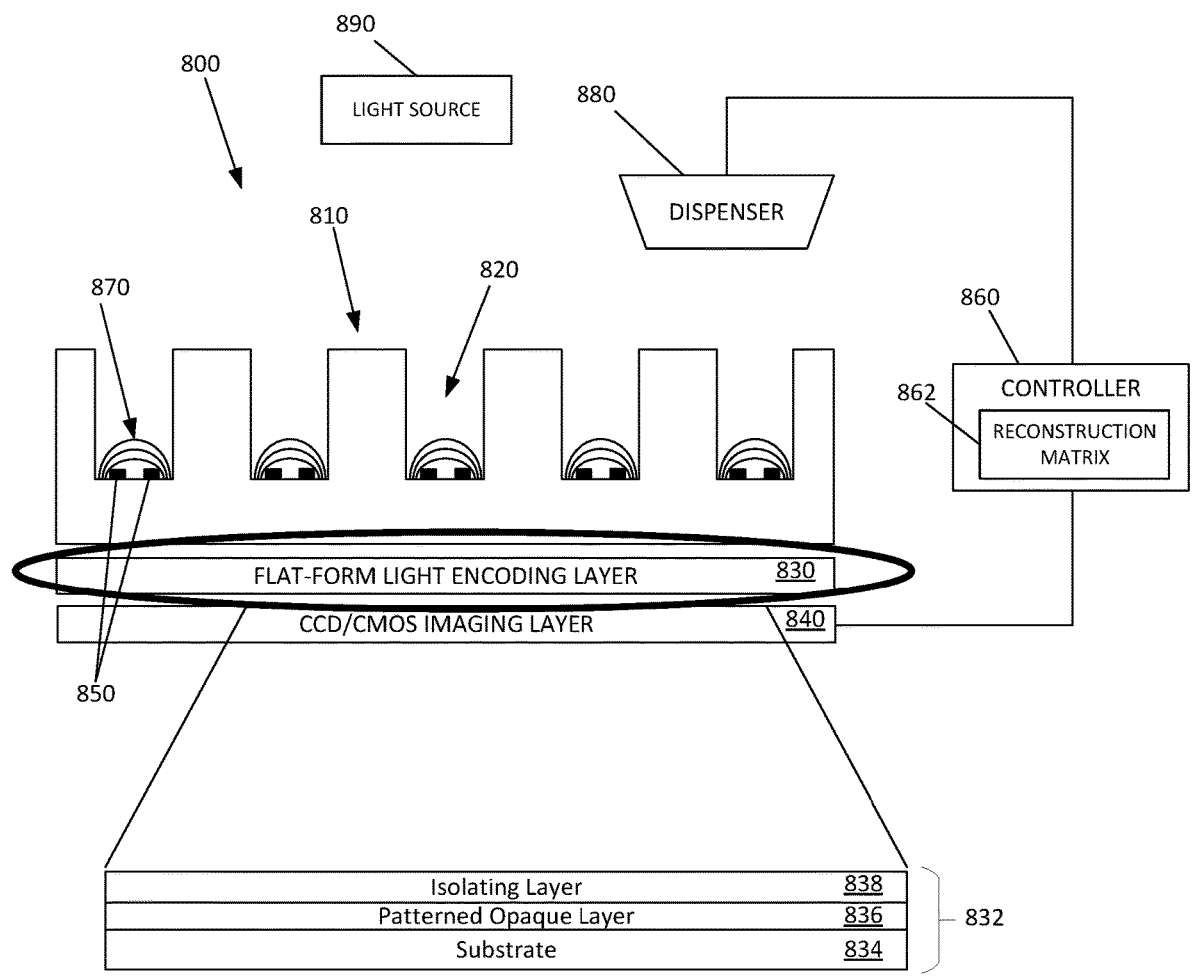
FIG. 8 is a schematic illustration of an example system for flat-form imaging.

Referring now to FIG. 8, a schematic illustration of an example system 800 for flat-form imaging is illustrated. The light encoding layer is either an amplitude mask used for lens-less computational imaging or by a meta-lens array. In both cases the distance between the light encoding layer and the imaging layer is between 10 microns and 1 mm. The distance between the electrode plane in the well plate and the light encoding layer is between 10 microns and 1 mm. This setup allows for a field of view as wide as the imaging sensor (several square millimeters). The example system 800 includes a well plate 810 which includes at least one well 820. The well plate 810 may be formed of any of a variety of materials such as, for example, plastics or glasses. In one example, the well plate 810 is formed of a non-reactive material, such as polypropylene. The well plate 810 may be of any practical size according to a desired application. For example, the well plate 810 may be sized to accommodate a specific number of wells 820. The well plate size can otherwise be matched to the imaging sensor size, or it can be bigger and the imaging device would be scanned across the well plate surface to image it completely.

In various examples, the well plate 810 of the example system 800 may be provided with any number of wells 820. The size and shape of each well 820 may be selected from any of a variety of sizes and shapes. In one example, the well 820 is cylindrical with a cross section that may be circular, rectangular, hexagonal or any of a variety of other shapes. In other examples, the well 820 is conical or other non-cylindrical shape. In one example, the well 820 is a circular cylinder with a diameter of between 1 mm and 100 mm.

Each well 820 may be provided for positioning of microscopic objects (not shown in FIG. 8) therein. As noted above, the microscopic objects may include biological material such as cells, for example. The wells 820 are formed to allow positioning of the microscopic objects at or near a bottom surface of the well 820 to facilitate imaging of the microscopic objects from beneath the well plate 810.

Each well 820 is provided with an array of electrodes 850 formed on the bottom surface of the well. As described above, in various examples, the array of electrodes 850 may be arranged in a concentric manner. The electrodes 850 may be provided with a voltage from an AC power source (not shown in FIG. 8). The AC power source may be coupled to a controller 860 which selectively provides voltage from the AC power source to the electrodes 850 in each well 820 of the well plate 810. As described above, the voltage from the AC power source provided to the electrodes generates a non-rotating, non-uniform electrical field 870.

The example system 800 of FIG. 8 is provided with a light encoding layer 830 positioned below the well plate 810 and an imaging layer 840 positioned below the light encoding layer 830. A light source 890 is positioned above the well plate 810 to illuminate the well plate 810. Thus, the light source 890 is positioned on one side of the well plate 810, and the light encoding layer 830 and the imaging layer 840 are positioned on a second, opposite side of the well plate 810.

Thus, the light encoding layer 830 is positioned to encode light from the light source 890 passing through the array of wells 820, as well as any microscopic objects therein. As noted above, in various example, the light encoding layer 830 is provided with a substantially flat form.

In one example, the flat-form light encoding layer 830 includes a lens-less, amplitude mask arrangement 832, as illustrated in the example of FIG. 8. The amplitude mask arrangement 832 is provided to encode the light passing through the well plate 810 for computational reconstruction of the encoded information. The amplitude mask arrangement 832 includes a substrate 834 to support a patterned opaque layer 836 and an isolating layer 838. Light passing through the well plate 810 is passed through the isolating layer 838 and onto the patterned opaque layer 836.

As noted above, the amplitude mask arrangement 832 can facilitate computational imaging. In this regard, computational imaging uses conversion of the incident light to sensor measurements. Rather than representing an image, the sensor measurements can be coupled with an appropriate algorithm or function to reconstruct an image. The algorithm or function may be determined through a calibration process.

In various examples, the amplitude mask arrangement 832 may be directly coupled to the well plate 810. For example, the amplitude mask arrangement 832 may form the bottom surface of the well plate 810. In this regard, the isolating layer 838 may serve to provide isolation (e.g., chemical isolation) between the microscopic objects and the patterned opaque layer. In various examples, the isolating layer 838 may be formed of or coated with a fluorosilane or fluorinated paralyne to allow the microscopic objects to be rotated to allow 3D imaging. Such isolation may prevent the microscopic objects from being affected by, for example, metals in the patterned opaque layer which may be toxic to the microscopic objects.

The pattern of regions on the patterned opaque layer 836 is a two-dimensional separable pattern to encode the light in 2-dimensional regions. Each region may be sized to provide a resolution in the captured image of between 3 microns and 100 microns. Thus, the light encoded by the amplitude mask arrangement 632 may be captured by the imaging layer 840 in the form of an M×N matrix of pixels. In various examples, the imaging layer 840 may include a CCD layer or a CMOS layer, each pixel being between 1 microns and 10 microns wide. As noted above, the pattern allows for a computational conversion of the encoded light to an image through an appropriate algorithm or function. Thus, the exact pattern formed on the patterned opaque layer 836 may be any feasible pattern.

In one example, the patterned opaque layer 836 is formed with a fused silica glass wafer with a thin film of chromium deposited thereon. The chromium is etched to form a pattern. In various example, the pattern is formed to provide a desired feature size which may correspond to a pixel in the imaging layer 840.

In some examples, the amplitude mask arrangement 832 may be replaced with a diffuser layer (not shown). The diffuser layer may include a layer of a material with a non-uniform optical density, such as a thin sheet of thermally cured polymer or any semi-transparent coating. Various examples of diffuser layers may be fabricated with cost-efficient methods, such as fiber deposition, spin-coating or the like. Such methods can achieve the desired result without the use of specialized equipment such as for photolithography. The non-uniform density of the diffuser layer can allow encoding of light which can be processed to produce a reconstructed image using, for example, a reconstruction matrix 862, as described below.

The image captured by the imaging layer 840 may be processed by a controller 860 coupled to the imaging layer 840. In various examples, the controller 860 may include a processor to execute various instructions. The controller 860 may be implemented as hardware, software, firmware, or a combination thereof. In one example, the controller 860 is implemented as software stored on a non-transitory computer-readable medium and includes instructions that may be executable by a processor.

The processing of the image from the imaging layer 840 may include translating the raw image from the imaging layer 840 by a reconstruction matrix 862. The reconstruction matrix 862 may be obtained through calibration of the light encoding layer 830, for example. Thus, an array of pixels from the imaging layer 840 representing the raw image may be multiplied by the reconstruction matrix 862 to obtain an array of pixels representing a reconstructed image. Thus, the flat-form light encoding layer 830 can facilitate imaging of a wide field of view simultaneously.

In the example system 800 of FIG. 8, the controller 860 is coupled to a dispenser 880. The dispenser 880 is provided to drop, or inject, objects such as cells into the various wells 820 of the well plate 810. In various examples, the dispenser 880 may be provided to drop a single cell at a time. The controller 860 may be coupled to the dispenser 880 to move the dispenser to a selected location corresponding to a selected well 820. In other examples, the system 800 may include a movable stage (not shown) supporting the well plate 810. In this regard, the controller 860 may coordinate movement of the movable stage and the timing of dropping of the cell from the dispenser 880 to drop the cell into a desired, or selected, well 820 in the well plate 810.

In some examples, the dispenser 880 may inject or drop additional material into the wells 820. For example, the dispenser 880 may be used to add stimuli onto cells already in the wells 820 to facilitate a reaction or other response that may be observed or imaged. In other examples, the dispenser 880 may add fluorescent dyes or other stains to facilitate the imaging.

Thus, as noted above, the example system 800 may be used to facilitate imaging of a wide field of view simultaneously. The wide field of view may include a large number of wells 820 of the well plate 810, for example, thus allowing various types of analyses.

Figure 9:
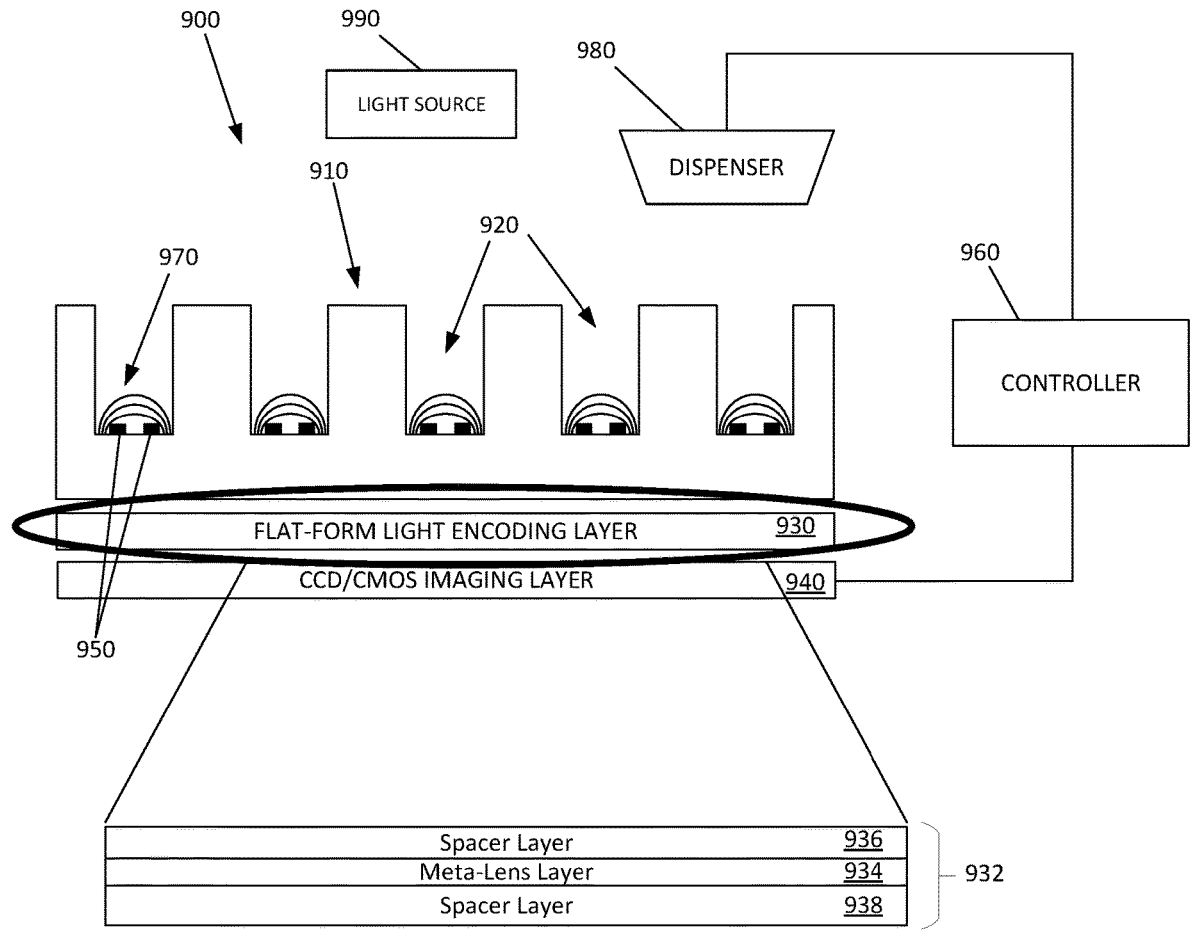
FIG. 9 is a schematic illustration of an example system for flat-form imaging.

Referring now to FIG. 9, a schematic illustration of another example system 900 for flat-form imaging is illustrated. The example system 900 of FIG. 9 is similar to the example system 800 described above with reference to FIG. 8 and includes a well plate 910 with various wells 920 to position microscopic objects, a light encoding layer 930, an imaging layer 940, a controller 960, a dispenser 980 and a light source 990.

Each well 920 is provided with an array of electrodes 950 formed on the bottom surface of the well. As described above, in various examples, the array of electrodes 950 may be arranged in a concentric manner. The electrodes 950 may be provided with a voltage from an AC power source (not shown in FIG. 9). The AC power source may be coupled to a controller 960 which selectively provides voltage from the AC power source to the electrodes 950 in each well 920 of the well plate 910. As described above, the voltage from the AC power source provided to the electrodes generates a non-rotating, non-uniform electrical field 970.

In the example system 900 of FIG. 9, the light encoding layer 930 is meta-lens arrangement 932. The meta-lens arrangement 932 includes a meta-lens layer 934 formed with an array of substantially flat lenses. In various examples, the array of lenses may be formed in a grid pattern corresponding to a grid of pixels groups in an image. In one example, the lenses in the meta-lens layer 934 are circular lenses with a diameter of between about 5 microns and about 200 microns. The thickness of each lens and the meta-lens layer 934 is between about 20 nm and about 1 microns. In various examples, the meta-lens layer 934 is provided with spacer layers 936, 938 to properly position the array of meta-lenses relative to the microscopic objects. For example, the spacer layers 936, 938 may provide the desired working distance for the meta-lenses in the layer 934.

In one example, the flat lenses of the meta-lens layer 934 may be lenses with a high numerical aperture in the visible wavelengths. In this regard, the lenses may have diffractive properties which provide a designed or desired focal length. In other examples, the flat lenses are formed as transmissive dielectric metalenses. Such metalenses may be formed with $TiO_2$ nanofins formed on a glass substrate, as described in Khorasaninejad, Mohammadreza et al. (Jun. 3, 2016) Metalenses at visible wavelengths: Diffraction-limited focusing and subwavelength resolution imaging. *Science Magazine*, Pages 1190-1194.

The meta-lens arrangement 932 may thus encode light from the light source 990 passing through the well plate 910. Each meta-lens in the meta-lens layer 934 may correspond to a group of pixels in an image captured by the imaging layer 940. The controller 960 can assemble the complete image with image pixels from the imaging layer 940.

Thus, the light encoding layer 930 with the meta-lens layer 934 provides flat-form imaging with a wide field of view. As described above with respect to FIG. 8, the example system 900 may thus be used to simultaneously monitor a large number of samples for reactions or culture growth, for example.

Figure 10:
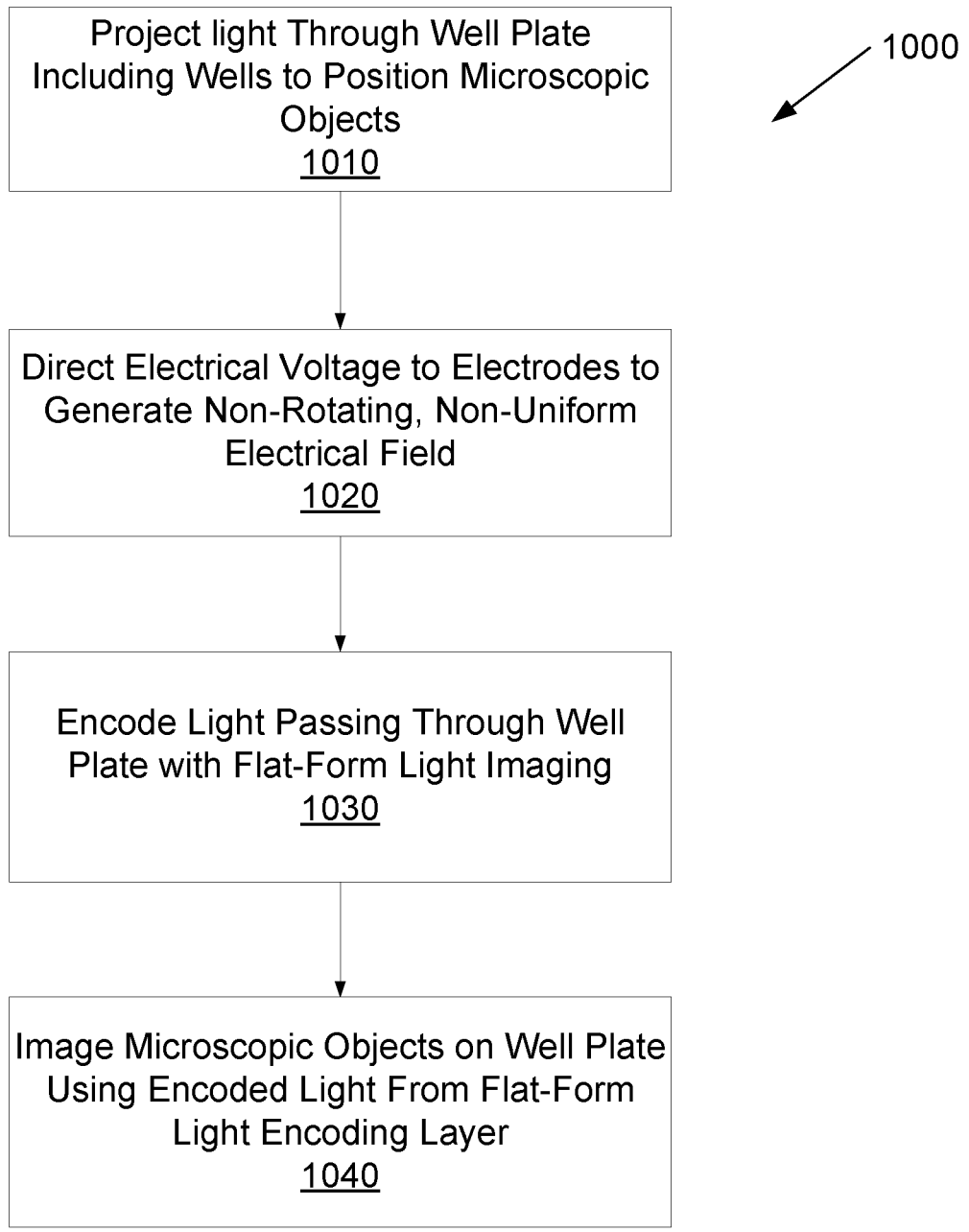
FIG. 10 is a flow chart illustrating an example method for flat-form imaging.

Referring now to FIG. 10, a flow chart illustrates an example method 1000 for flat-form imaging. The example method 1000 includes projecting light through a well plate having microscopic objects positioned thereon (block 1010). As noted above, in various examples, the well plate may include an array of wells.

The example method 1000 further includes directing electrical voltage to electrodes positioned within the wells (block 1020). The electrical voltage is to generate a non-rotating, non-uniform electrical field. The electrical field can rotate the microscopic object in the electrical field, as described above in the example of FIG. 4.

The example method 1000 further includes encoding light passing through the sampling layer with a substantially flat-form light encoding layer (block 1030). In various examples, the light encoding layer may include an amplitude mask arrangement, as described above with reference to FIG. 8, or a meta-lens arrangement, as described above with reference to FIG. 9, for example. The flat-form encoding layer provides a large field of view to facilitate encoding of light passing through a large number of samples, for example.

The example method 1000 further includes imaging the microscopic objects on the sampling layer using encoded light from the flat-form light encoding layer (block 1040). As noted above, a CCD device or a CMOS device may be used to capture an image using the encoded light from the flat-form light encoding layer.

Thus, the example systems described above provide an efficient and cost-effective imaging of a large number of samples. The use of flat-form light encoding allows imaging within a large field of view, allowing the large number of samples to be simultaneously monitored.

The foregoing description of various examples has been presented for purposes of illustration and description. The foregoing description is not intended to be exhaustive or limiting to the examples disclosed, and modifications and variations are possible in light of the above teachings or may be acquired from practice of various examples. The examples discussed herein were chosen and described in order to explain the principles and the nature of various examples of the present disclosure and its practical application to enable one skilled in the art to utilize the present disclosure in various examples and with various modifications as are suited to the particular use contemplated. The features of the examples described herein may be combined in all possible combinations of methods, apparatus, modules, systems, and computer program products.

It is also noted herein that while the above describes examples, these descriptions should not be viewed in a limiting sense. Rather, there are several variations and modifications which may be made without departing from the scope as defined in the appended claims.

What is claimed is:

1. An apparatus, comprising:
a well plate having an array of wells;
a light encoding layer positioned under the well plate, the light encoding layer to encode light passing through a microscopic object in at least one well of the array of wells, wherein the light encoding layer has a substantially flat form and is to provide a wide field of view to encompass microscopic objects in the well plate;
an imaging layer to capture an image of the well plate, the image being encoded by the light encoding layer;
an array of electrodes positioned on a surface of a bottom floor of the at least one well; and
a controller to direct electrical voltage to the electrodes to generate a non-rotating, non-uniform electrical field, the electrical field being to rotate an object in the electrical field.

2. The apparatus of claim 1, wherein the electric field is to generate an electrical torque on the object when the object is near an electrode so as to rotate the object about a rotational axis parallel to the edge of the electrode.

3. The apparatus of claim 1, wherein the rotational axis is normal to the imaging layer.

4. The apparatus of claim 1, wherein the light encoding layer includes a flat-form, lens-less layer to facilitate computational imaging.

5. The apparatus of claim 4, wherein the flat-form lens-less layer includes at least one of an amplitude mask or a diffuser.

6. The apparatus of claim 1, wherein the light encoding layer includes a substantially flat array of lenses.

7. The apparatus of claim 1, wherein the imaging layer includes at least one of a charge-coupled device (CCD) or a complementary metal-oxide semiconductor (CMOS) device.

8. A system, comprising:
a well plate including an array of wells;
an array of electrodes formed on a bottom surface of each well in the array of wells;
an alternating current (AC) power source coupled to each electrode in the array of electrodes;
a light encoding layer positioned below the well plate, the light encoding layer to encode light passing through the array of wells, wherein the light encoding layer has a substantially flat form and is to provide a wide field of view to encompass microscopic objects in the well plate;
an imaging layer to capture the encoded image from the light encoding layer; and
a controller to:
direct electrical voltage to the electrodes to generate a non-rotating, non-uniform electrical field, the electrical field being to rotate an object in the electrical field;
cause the imaging layer to capture an encoded image of the object in at least two rotated positions; and
generate a reconstructed image based on the encoded images.

9. The system of claim 8, wherein the electric field is to generate an electrical torque so as to rotate the object about a rotational axis.

10. The system of claim 8, further comprising:
a dispenser to dispense samples into the array of wells.

11. The system of claim 8, wherein the controller is to generate the reconstructed image via application of at least one transformation matrix to the encoded image.

12. The system of claim 8, wherein the controller is to monitor growth of samples in the array of wells.

13. A method, comprising:
projecting light through a well plate, the well plate having wells to position microscopic objects therein;
directing electrical voltage to electrodes positioned within the wells to generate a non-rotating, non-uniform electrical field, the electrical field being to rotate the microscopic object in the electrical field;

encoding the light passing through the well plate with a substantially flat-form light encoding layer, wherein the substantially flat-form light encoding layer provides a wide field of view to encompass the microscopic objects in the well plate; and imaging the microscopic objects on the well plate using encoded light from the flat-form light encoding layer.

14. The method of claim 13, wherein the substantially flat-form light encoding layer is a lens-less layer to facilitate computational imaging.

15. The apparatus of claim 1, wherein the array of electrodes is arranged in a concentric formation.

16. The apparatus of claim 15, wherein the array of electrodes is arranged as rectangular electrodes.

17. The system of claim 8, wherein the light encoding layer comprises an amplitude mask with a patterned opaque layer.

18. The system of claim 17, wherein the amplitude mask further comprises an isolating layer.

19. The system of claim 8, wherein the light encoding layer comprises a diffuser with a non-uniform optical density.

20. The system of claim 8, wherein the light encoding layer comprises a flat array of meta-lenses.

* * * * *